(12) United States Patent
Monod (10) Patent No.: US 8,703,444 B2
(45) Date of Patent: Apr. 22, 2014

(54) ***PICHIA PASTORIS* DEFICIENT IN ENDOGENOUS SECRETED PROTEASE**

(75) Inventor: Michel Monod, Lausanne (CH)

(73) Assignee: Centre Hospitalier Universitaire Vaudois (CHUV), Lausanne (CH)

( * ) Notice: Subject to any disclaimer, the term of this patent is extended or adjusted under 35 U.S.C. 154(b) by 0 days.

(21) Appl. No.: 13/515,577

(22) PCT Filed: Dec. 13, 2010

(86) PCT No.: PCT/IB2010/055777
§ 371 (c)(1),
(2), (4) Date: Jul. 16, 2012

(87) PCT Pub. No.: WO2011/073883
PCT Pub. Date: Jun. 23, 2011

(65) Prior Publication Data
US 2012/0295307 A1    Nov. 22, 2012

(51) Int. Cl.
*C12N 9/60* (2006.01)

(52) U.S. Cl.
USPC ..................... 435/69.1; 435/254.23

(58) Field of Classification Search
USPC ......................................... 435/192
See application file for complete search history.

(56) References Cited

U.S. PATENT DOCUMENTS 5,691,166 A    11/1997    Gleeson et al. .............. 435/69.1

OTHER PUBLICATIONS

Monod. Secreted proteases from dermatophytes. Mycopathologia. 166: 285-294, 2008.*
De Schutter, K., et al. (2009) "Genome sequence of the recombinant protein production host *Pichia pastoris*" Nature Biotechnology, vol. 27, No. 6, p. 561-566.
Macauley-Patrick, S., et al. (2005) "Heterologous protein production using the *Pichia pastoris* expression system" Yeast, 22:249-270.
Salamin, K., et al. (2010) "Secretion of an endogenous subtilisin by *Pichia pastoris* strains GS115 and KM71" Applied and Environmental Microbiology, vol. 76, No. 13, pp. 4269-4276.
Sinha, J., et al. (2004) "Causes of proteolytic degradation of secreted recombinant proteins produced in methylotrophic yeast *Pichia pastoris*: case study with recombinant ovine interferon-$\gamma$" Biotechnology and Bioengineering, vol. 89, No. 1.
(2009) "SubName: Full=Vacuolar proteinase B (YscB), a serine protease of the subtilisin family;" XP002631769.
International Search Report and Written Opinion May 4, 2011.

* cited by examiner

*Primary Examiner* — Tekchand Saidha
*Assistant Examiner* — Rama P Ramanujam
(74) *Attorney, Agent, or Firm* — Harness, Dickey & Pierce, P.L.C.

(57) ABSTRACT

The present invention relates to micro-organisms and to methods of producing proteins. More specifically, the inventions relates to a host cell useful for the expression of heterozygous proteins in which the host cell, *Pichia pastoris*, has been genetically modified so that the gene for endogenous secreted subtilisin Sub2 protease is completely or partially inactivated.

6 Claims, 6 Drawing Sheets

Figure 1

1 : SDS-PAGE buffer as a control
2 : GS115-*sub2*
3 : KM71 -*sub2*
4 : GS115
5 : KM71

Figure 2

1 : GS115
2 : KM71
3 : KM71-*SUB1*
4 : KM71-*SUB2*

Figure 3

1 : GS115
2 : GS115-*sub2* transformed with pKJ113-DPPIV
3 : GS115-*DPPIV*
4 : GS115-*DPPIV* transformed with pKS1
5 : GS115-*sub2* transformed with pKJ113-LAP1
6 : GS115-*LAP1*
7 : GS115-*LAP1* transformed with pKS1
8 : GS115-*sub2*

Figure 4

1 : 10ng
2 : 3ng
3 : 1ng
4 : 300pg
5 : 100pg
6 : 30pg
7 : GS115 (10μl culture supernatant)

PICHIA PASTORIS DEFICIENT IN ENDOGENOUS SECRETED PROTEASE

PRIORITY STATEMENT

This application is a national phase under 35 U.S.C. §371 of PCT International Application No. PCT/IB2010/055777 which has an International filing date of 13 Dec. 2010, which claims priority under 35 U.S.C. §119 to PCT International Application No. PCT/IB2009/055729, filed on 14 Dec. 2009. The contents of each application recited above are incorporated herein by reference in their entirety.

FIELD OF THE INVENTION

The present invention relates to micro-organisms and to methods of producing proteins. More specifically, the inventions relates to a host cell useful for the expression of heterologous proteins in which the host cell, Pichia pastoris, has been genetically modified.

BACKGROUND OF THE INVENTION

The yeasts have received broad attention in recent years, and offer some advantages of the prokaryotic system, such as simple genetic manipulation and rapid growth. The yeast organisms are able to make post-translational protein modifications typical of eukaryotic cells. Among those employed as expression systems of interest is Pichia pastoris, which has received wide acceptance for the production of biopharmaceuticals, since it is capable of doing some post-translational process, such as glycosylation, so very similar to mammals.

One of the most important features of Pichia pastoris is its ability to grow in culture medium containing methanol as the sole source of carbon. The first step in the use of methanol is the oxidation of this, leading to the formation of formaldehyde and hydrogen peroxide, a reaction catalyzed by the enzyme alcohol oxidase. Pichia pastoris has two genes that encode for alcohol oxidase, AOX1 and AOX2, but only the former is heavily regulated by methanol while the second is expressed in low quantities. When Pichia pastoris grows in the presence of glycerol, glucose or ethanol, the alcohol oxidase enzyme is not found, however, in the presence of methanol, the alcohol oxidase enzyme 1 (AOX1) may reach 35% of total cellular proteins. The control of AOX1 gene expression occurs at transcriptional level. The promoter of the gene AOX1 has been widely used for the construction of expression vectors of Pichia pastoris for being strong and highly adjustable, which reduces the possibility of toxic proteins harming the cell growth. These vectors are integrative type, allowing the stabilization of the exogenous gene message in the genome of Pichia pastoris.

Another major advantage of expressing heterologous proteins or polypeptides as secreted recombinant proteins in Pichia pastoris is that Pichia pastoris secretes very low levels of native proteins. More interesting, there have been no reports of extracellular proteases in Pichia pastoris and studies suggest that most of the proteases active in Pichia pastoris are intracellular and not secreted (Jayanta Sinha et al., Biotechnology and Bioengineering, 89:102-112, 2005).

Still another important feature is that the expression of heterologous proteins or polypeptides in Pichia pastoris has shown high levels of production when grown at high cell densities in simple defined medium. Indeed, the strong promoter, coupled with the high cell density fermentation, has allowed production of heterologous proteins or polypeptides at high concentration.

Furthermore, it is known from U.S. Pat. No. 5,691,166 (Martin A. Gleeson et al.) that while growth at high cell density enables the production of heterologous proteins or polypeptides in remarkably high yields, growth at high cell density also provides for a relatively high level of vacuolar proteases in the fermentation media (since about 1% of cells typically undergo lysis during yeast fermentation, the high cell density process is accompanied by the release of substantial quantities of cellular material into the media, including vacuolar proteases). Therefore, during the production of heterologous proteins or polypeptides in a high cell density process, some of the secreted heterologous proteins or polypeptides produced by Pichia could be subjected to substantial proteolysis.

Indeed it is well known that generally in yeast, the major store of proteolytic activity is located within the lumen of the vacuolar compartment (Jones, Methods Enzymol 194:428-453, 1991). These proteases are released into the fermentation broth by spontaneous and inevitable cell lysis. Although vacuolar proteases are required for several developmental transitions in the life cycle of yeast cells (e.g., sporulation), they are dispersible for vegetative growth. The majority of vacuolar proteases are synthesized and transported through the secretory pathway as enzymatically inactive zymogens (Klionsky et al., Microbiol. Rev. 54:266-292, 1990; Raymond et al., Int. Rev. Cytol. 139:59-120, 1992). They are proteolytically activated by the combined action of proteinase A, the product of the PEP4 gene, and proteinase B, the product of the PRB1 gene.

Many other documents of the prior art also disclose that the proteolytic degradation of secreted heterologous proteins or polypeptides in Pichia pastoris is indeed due to the release of proteases in the culture medium caused by degradation of the cell membrane due to cell lysis in high cell density fermentation (Zhengjun Li et al., Protein Expression and Purification, 21:438-445, 2001; Jayanta Sinha et al., Biotechnology and Bioengineering, 89:102-112, 2005; Diethard Mattanovich et al., Microbial Cell Factories, 8:29, 2009).

In view of the excellent performance of the Pichia-based expression system for the production of many heterologous proteins or polypeptides, it would be desirable to reduce or eliminate the proteolytic activities of Pichia pastoris. This would reduce the likelihood of degradation of protease-sensitive proteins when produced in recombinant Pichia hosts, allow an enhanced ability to express and recover heterologous proteins or polypeptides in substantially intact form and avoid endogenous protease contaminants, further allowing easier purification of heterologous proteins, such as heterologous proteases.

Various techniques attempt to deal with this problem of the proteolytic degradation of secreted heterologous proteins or polypeptides in Pichia pastoris. For example, one could modify the conditions under which recombinant Pichia strains are grown so as to inhibit protease activity. This could be accomplished, for example, by adjusting the pH of the medium sufficiently to inhibit the action of various proteases. This approach, however, may affect the ability of the host organism to express certain heterologous proteins or polypeptides (as well as the stability of the resulting protein, once expressed). Alternatively it is possible to add protease inhibitors.

Another known example is the use of protease-deficient strains. Some vacuolar protease-deficient strains of Pichia are already available, such as Pichia methanolica strain disclosed in WO 99/14347 (Zymogenetics, Inc.), which is deficient in proteinase A or proteinase B activity, or Pichia pastoris strains SMD1168, SMD1163 or SMD1165, which posses a substantial decrease in or elimination of proteinase A, carboxypeptidase Y and/or proteinase B activities.

However, it is not easy to create protease-deficient strains. Indeed the proteolytic processes in eukaryotic organisms are quite complicated and involved in cell metabolism. Thus, it is not possible to predict if elimination and/or modification of one or more of the enzyme(s) that are involved in proteolytic processing pathways will have an impact on the viability of the host cells, and/or the stability of the secreted heterologous protein or polypeptide.

The drawback to each of the above-mentioned attempts is that the degradation of secreted heterologous proteins or polypeptides in *Pichia pastoris* is still observed.

The problem of the degradation of secreted heterologous proteins or polypeptides in *Pichia pastoris* remains unsolved. Surprisingly the Applicant was able to overcome this problem in the present invention.

SUMMARY OF THE INVENTION

The Applicant has shown that, contrary to what is currently established in the prior art, the proteolytic activity observed in *Pichia pastoris* culture medium was due to a secreted subtilisin Sub2, a serine protease of the subtilisin family and not to cell lysis and/or vacuolar proteases.

Thus the present invention provides a *Pichia pastoris* cell suitable for the production of heterologous polypeptides, characterized in that said cell has been modified by recombinant DNA technology so that the gene for endogenous subtilisin Sub2 encoded by the DNA sequence comprising SEQ ID NO: 1 or variants or fragments thereof is completely or partially inactivated.

The invention further provides a method of producing a heterologous polypeptide in the *Pichia pastoris* cell according to the invention, said method comprising:
  (a) introducing into said cell a nucleic acid sequence encoding for a polypeptide;
  (b) cultivating the cell of step (a) in a culture medium under conditions suitable for producing a polypeptide; and
  (c) recovering a polypeptide.

The invention also provides method for improving the production of heterologous polypeptides by a *Pichia pastoris* cell comprising inactivating completely or partially the gene for endogenous subtilisin Sub2 encoded by the DNA sequence comprising SEQ ID NO: 1 or variants or fragments thereof in said *Pichia pastoris* cell.

Another aspect of the invention is a method for obtaining the *Pichia pastoris* cell of the invention, wherein the inactivation of the subtilisin Sub2 gene is obtained by:
  i) cloning of the subtilisin Sub2 gene from *Pichia pastoris*,
  ii) producing a DNA construct comprising the subtilisin Sub2 gene, wherein a part of said gene has been substituted, deleted, or extra DNA has been inserted within said subtilisin Sub2 gene,
  iii) transforming said *Pichia pastoris* cell with the DNA constructs, and
  iv) isolating transformants from which:
    1) no subtilisin Sub2 activity can be determined;
    2) a reduced level of subtilisin Sub2 activity can be determined; or
    3) subtilisin Sub2 having lost its function can be obtained.

Further aspect of the invention is a method for obtaining the *Pichia pastoris* cell of the invention, wherein the inactivation of the subtilisin Sub2 gene is obtained by using anti-sense technology, said method comprising:

i) construction of an expression plasmid resulting in the synthesis of a RNA molecule complementary to the mRNA transcribed from the subtilisin Sub2 gene; transformation of said *Pichia pastoris* cell with said expression plasmid and a suitable marker;
  iii) selection of transformants using said marker; and
  iv) screening the selected transformants presenting reduction in the synthesis of the subtilisin Sub2 product.

DETAILED DESCRIPTION OF THE INVENTION

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components.

As used in the specification and claims, the singular form "a", "an" and "the" include plural references unless the context clearly dictates otherwise.

The methylotrophic yeast *Pichia pastoris* has been used successfully to express a wide range of heterologous proteins; one of the main interests being that *Pichia pastoris* secretes low levels of native proteins. Therefore it is well known that *Pichia pastoris* is a powerful tool to individually produce numerous secreted heterologous proteases as recombinant proteins in substantial amounts, without endogenous secreted proteases (contaminating proteases). This is very useful when highly purified proteases are needed to analyze for example different steps in protein and peptide digestion. The availability of recombinant proteases assisted many studies in the fields of secreted protease biochemistry, crystallography and clinical microbiology. Using a reverse genetic approach (from gene to protein), it was also possible to synthesize proteases which were revealed by genome sequencing, but which were not yet discovered and remained so far putative.

The Applicant used *Pichia pastoris* to produce recombinant leucine aminopeptidases, dipeptidyl-pepptidases and trieptidyl-pepptidases of the sedolisin family. Surprisingly and contrary to what has been known and expected, the Applicant realized that purified fractions of the above-mentioned proteases contained endoproteolytic activity. Thus in the present invention, the Applicant identifies and characterizes a contaminating protease of the subtilisin family which is secreted in minor amount by *Pichia pastotris* during growth in methanol medium. Indeed, the Applicant has surprisingly found that *Pichia pastoris* genome harbours two genes encoding serine proteases of the subtilisin family (Sub): Sub1 codes for the vacuolar Proteinase B which is not secreted in culture medium, whereas Sub2 codes for a subtilisin which is secreted in low amount (3 ng/ml culture medium of cells at OD 50 in methanol medium).

Figure 1:
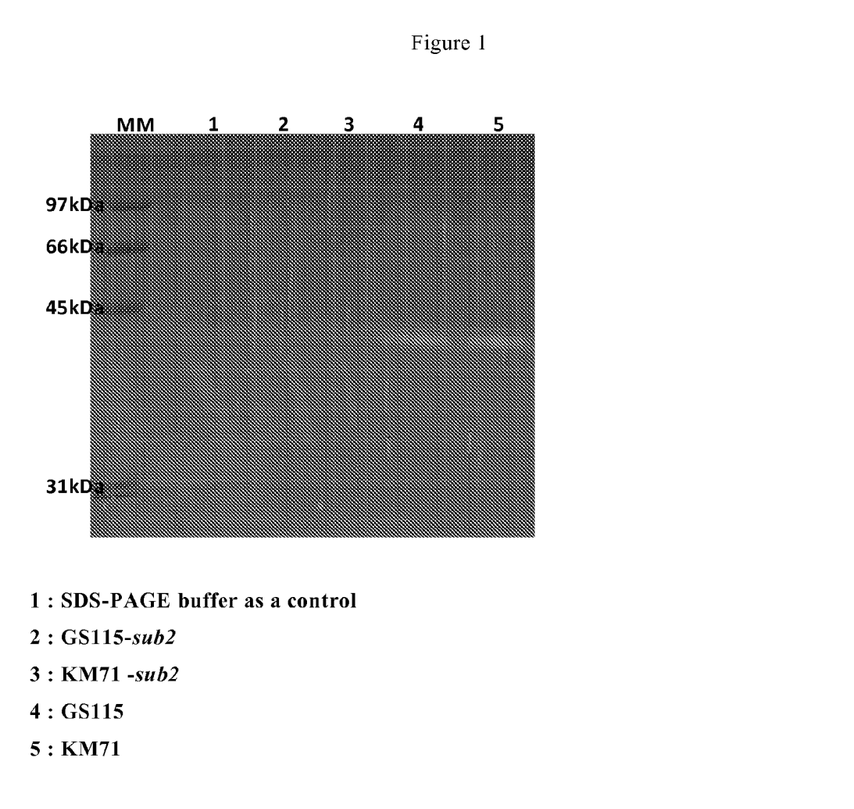
FIG. 1: Native secreted subtilisin production by *P. pastoris* GS115 and KM71 and derivative strains

Secreted proteolytic activity from *Pichia pastoris* GS115 and KM71 has been studied. Two distinct gelatinolytic activities in *Pichia pastoris* cell culture supernatant were detected in SDS-PAGE gels containing gelatin as a substrate. One protease (proteolytic component) showed a distinct band and had an apparent molecular mass of 40 kDa (FIG. 1). A second protease appeared as large faint band, and had an apparent molecular mass comprised between 55 and 70 kDa. The 40-kDa protease was completely inhibited when the gel was incubated in the presence of 1 mM PMSF, but not in the presence of 1,10-phenanthroline and EDTA, suggesting that it was a serine protease. The 55-70 kDa protease was inhibited neither by PMSF nor by the above mentioned chelating agents. Both gelatinolytic activities were stronger at pH 7.0 than at pH 4.0.

In a first attempt, the Applicant searched to disrupt the gene encoding vacuolar protease B (Prb) in GS115 strain. Protease B is a serine protease of the subtilisin family and was postulated to be secreted by *Pichia pastoris*. A gene encoding the putative *Pichia pastoris* Prb (ppPRB) was cloned from a *Pichia pastoris* genomic library as described in material and methods using *Saccharomyces cerevisiae* PRB DNA as a probe. ppPRB targeted disruption did not allow to abolish gelatinolytic activity in *Pichia pastoris* cell culture supernatant. Therefore the Applicant searched to clone another gene encoding a subtilisin for subsequent disruption.

*Pichia pastoris* transformants producing various heterologous proteases were found to secrete more Sub2 than GS115 or KM71. This observation contrasts with previous findings made in *A. niger*, *Trichoderma reesei* and *S. cerevisiae*. Endoplasmic reticulum (ER)-associated stress generated by expression of heterologous secreted proteins or polypeptides was found to lead to the transcriptional down-regulation of some genes encoding secreted proteins, an effect termed repression under ER stress (RESS) which may be independent of the UPR.

*Pichia pastoris* Cell

Thus the present invention provides a *Pichia pastoris* cell suitable for the production of heterologous polypeptides, characterized in that said cell has been modified by recombinant DNA technology so that the gene for endogenous subtilisin Sub2 encoded by the DNA sequence comprising SEQ ID NO: 1 or variants or fragments thereof is completely or partially inactivated.

The *Pichia pastoris* cell of the invention is derived from any *Pichia pastoris* cell conventionally used for the heterologous expression of polypeptides or proteins. Preferably the *Pichia pastoris* cell of the invention is derived from the parental cell selected from the group comprising wild type *Pichia pastoris* cell, *Pichia pastoris* GS115 strain, *Pichia pastoris* SMD1168 and SMD1168H strains, *Pichia pastoris* KM71 strain, *Pichia pastoris* SMD1163 strain or *Pichia pastoris* SMD1165 strain.

The recombinant DNA technology is specific or random mutagenesis or specific deletion, insertion and/or substitution in DNA sequence encoding the gene for endogenous subtilisin Sub2, gene disruption or gene replacement techniques, anti-sense techniques, or a combination thereof.

The *Pichia pastoris* cell of the present invention can further comprise a DNA sequence encoding for a heterologous polypeptide of interest. Preferably the heterologous polypeptide is selected from the group consisting of therapeutic proteins, antibodies or enzymes.

Subtilisin Sub2

In the context of this invention a subtilisin Sub2 protease is a serine protease having the activity at pH 6-9.5. The subtilisin Sub2 protease is a *Pichia pastoris* subtilisin Sub2 protease (Sub2) encoded by a cDNA sequence comprising SEQ. ID. No. 1, or variants, or fragments thereof or a sequence homologous thereto.

As used herein, the term "DNA" is intended to include nucleic acid molecules or DNA molecules (such as cDNA or genomic DNA), RNA molecules (such as mRNA), analogs of the DNA or RNA generated using nucleotide analogs, derivatives, variants fragments and homologs thereof. The nucleic acid molecule may be single-stranded or double-stranded.

TABLE 1

SEQ ID NO: 1

ATGAAAATTATCAGATTAGCATCAGTGGCTACCGTGGCTACCCTGGCACA

CTCGCTTTTGATACCATCTCTTGACCAATTGAATATCCAATTGCCGTTTT

CCTTGCCCCATCATACTGAGTCTCCATCGCTGAAATTACAGGGATCTAAC

CCATTTGAATCTTCCACAGTGAGACCCGACCCTATCCAGATATATTCGAC

TGGATATAAGGTGATTGAGAACTCCTATATTGTCACTGTAGACAGTTCCA

TCACTGATTCGGAACTTCAGCAGCTTTATGACTACATTAAAGGTGGATAC

GAATTCATGTTGAACAATGAAGACCCCTTTTTCGTTGCCATGGGTATTAA

GAGACTACCCAAGCATTCTTTGTTTGAACCTTTCAGTATCGGTGACTCCA

TGAAAGGCTTTGTCGGTTTCTTTCCACCAAGACTAGTTGAAAAACTGGCC

TCTATGGACCTTCCTATAGTGGCTATCGAGGCAGATTCAGTAGTCCATTC

GACAAAAGAGTACGCAGTTGACGAACATGTAACCTGGGGTTTGGCTAGAA

TTTCCCAGAGGCAAACACTAGATACCAATAGAAATTATATATACCATGTC

GATGGTGGCAAAAATGTTACCGCCTATGTCATCGACACTGGTATTTTTGT

TGACCATGAACAGTTTGAAAAGCGGGCTCGTTGGGGTGCAACTATCCCAT

TTGGGGACGTTGACAAGGATGCCAATGGACACGGAACTCATGTGGCTGGT

ACAATCGGTTCCGCAAAATATGGTGTGGCTAAACAGACTTCACTGGTGGC

AGTAAAGGTGCTCAACTCTGATGGGACTGGCACCCTTTCAGATGTCATTA

TABLE 1-continued

```
AAGGCATTGAGTTTGTGGTCAAAGACCACAAGAGCTCAAGGGGCAAGTCT

AAGGGCTCTGTTGCTAACATGTCCTTAGGTGGTGGTCTGTCAGTTGCTCT

CACATACGCTGTAAATGCTGCTGTTGATAATGGCATCCACTTTGCCGTAG

CCGCTGGAAATGACAATGCTAACGCTTGCAGTTACTCTCCAGCAAATTCA

GCTAAGGCAATCACTGCAGCTGCCTCTACTGTCGAGGACGAACGTGCGTT

CTTCAGTAACTGGGGTACCTGTGTGGACGTCTTTGCCCCAGGGTATCTTA

TTGAGTCCACCTACATTGGCCTTCCAACCTCCACAAGAGTTCTTTCGGGT

ACTTCGATGGCCTCTCCACACGTTGCCGGTCTTTTGAGTTACTACCTCTC

TCTACAACCCGGGCATGAATCGCAATATAACTCCGGTGACTCATTGACCC

CAGCTCAACTAAAAGCTAGGATTTTGAGTTTCAGTACCAAGGATGTACTT

GATGACTCGGATCTAAACTATGGCACTCCTAACTTGCTAATCTACAACTC

AAGAGACAACATTACTGAATTTTGGGATTATTAA
```

As used herein DNA sequence homology is determined as the degree of identity between the two sequences indicating a derivation of the first sequence from the second. Identity as known in the art and used herein, is a relationship between two or more nucleic acid sequences, as determined by comparing the sequences. It also refers to the degree of sequence relatedness between nucleic acid sequences, as the case may be, as determined by the match between strings of such sequences. Identity and similarity are well known terms to one skilled in the art and they can be calculated by conventional methods (for example see Computational Molecular Biology, Lesk, A. M. ed., Oxford University Press, New York, 1988; Biocomputing: Informatics and Genome Projects, Smith, D. W. ed., Academic Press, New York, 1993; Computer Analysis of Sequence Data, Part I, Griffin, A. M. and Griffin, H. G. eds., Humana Press, New Jersey, 1994; Sequence Analysis in Molecular Biology, von Heinje, G. Academic Press, 1987; and Sequence Analysis Primer, Gribskov, M. and Devereux, J. eds. M. Stockton Press, New York, 1991, Carillo, H. and Lipman, D., SIAM J. Applied Math. 48:1073, 1988).

The homologous DNA sequence exhibits a degree of identity preferably of at least 50%, 55%, 60%, 65%, 70%, 75%, 80%, or 85% with SEQ ID NO:1; more preferably 90% identity with SEQ ID NO:1; and most preferably at least 95%, 96%, 97%, 98%, or 99% identity with SEQ ID NO:1.

The invention also includes variant DNA sequences of SEQ ID NO: 1, which still encode a protease that maintains Sub2 biological activity, or a fragment of SEQ ID NO: 1. With "variants" or "variants of a sequence" is meant a nucleic acid sequence or DNA sequence that vary form the reference sequence by conservative nucleic acid substitutions, whereby one or more nucleic acids are substituted by another with same characteristics. Variants encompass as well degenerated sequences, sequences with deletions and insertions, as long as such modified sequences exhibit the same biological activity as the reference sequence (i.e. encoding a protease having Sub2 biological activity).

The invention further includes DNA sequence whose sequence is complementary to SEQ ID NO: 1, including DNA fragments that are complementary to SEQ ID NO:1 as well. The complementary DNA sequence is sufficiently complementary to SEQ ID NO:1 that it can bind (via hydrogen bond) with little or no mismatches to SEQ ID NO:1, thereby forming a stable duplex. As used herein, the term "complementary" refers to Watson-Crick or Hoogsteen base pairing between nucleotide units of a nucleic acid molecule.

Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice.

A DNA or nucleic acid fragment encoding a biologically-active fragment of Sub2 protease can be prepared by isolating a fragment SEQ ID NO: 1 that encodes a protease having a biological activity of Sub2 protease of the invention (the biological activity of Sub2 protease of the invention is described above), expressing the encoded portion of Sub2 protease (for example, by recombinant expression in vitro) and assessing the activity of the encoded fragment of protease. As used herein, the term "biological activity" refers to the natural or normal function of Sub2 protease of the invention, for example the ability to degrade proteins.

Derivatives are nucleic acid sequences or amino acid sequences formed from the native compounds either directly or by modification or partial substitution. Analogs are nucleic acid sequences or amino acid sequences that have a structure similar to, but not identical to, the native compound but differ from it with respect to certain components or side chains. Analogs may be synthetic or from a different evolutionary origin and may have a similar or identical biological activity compared to wild type. Homologs or orthologs are nucleic acid sequences or amino acid sequences of a particular gene that are derived from different species. Derivatives and analogs may be full length or other than full length, if the derivative or analog contains a modified nucleic acid or amino acid, as described herein. Derivatives or analogs of the nucleic acids or proteins of the invention include, but are not limited to, molecules comprising regions that are substantially homologous to the nucleic acids or proteins of the invention as described herein.

Moreover, DNA sequences encoding Sub2 protease of the invention from other species, and, thus, that have a DNA sequence that differs from SEQ ID NO: 1 are intended to be within the scope of the invention. DNA molecules corresponding to natural allelic variants and homologues of Sub2 protease cDNAs of the invention can be isolated based on their homology to Sub2 protease DNA disclosed herein using the fungal cDNAs, or a portion thereof, as a hybridization probe according to standard hybridization techniques under stringent hybridization conditions.

The subtilisin Sub2 protease is a *Pichia pastoris* subtilisin Sub2 protease (Sub2) having the amino acid sequence comprising the sequence SEQ ID NO:2, or a sequence homologous thereto.

TABLE 2

SEQ ID NO: 2

```
MKIIRLASVA TVATLAHSLL IPSLDQLNIQ LPFSLPHHTE

SPSLKLQGSN PFESSTVRPD PIQIYSTGYK VIENSYIVTV

DSSITDSELQ QLYDYIKGGY EFMLNNEDPF FVAMGIKRLP

KHSLFEPFSI GDSMKGFVGF FPPRLVEKLA SMDLPIVAIE

ADSVVHSTKE YAVDEHVTWG LARISQRQTL DTNRNYIYHV

DGGKNVTAYV IDTGIFVDHE QFEKRARWGA TIPFGDVDKD
```

TABLE 2-continued

```
ANGHGTHVAG TIGSAKYGVA KQTSLVAVKV LNSDGTGTLS

DVIKGIEFVV KDHKSSRGKS KGSVANMSLG GGLSVALTYA

VNAAVDNGIH FAVAAGNDNA NACSYSPANS AKAITAAAST

VEDERAFFSN WGTCVDVFAP GYLIESTYIG LPTSTRVLSG

TSMASPHVAG LLSYYLSLQP GHESQYNSGD SLTPAQLKAR

ILSFSTKDVL DDSDLNYGTP NLLIYNSRDN ITEFWDY
```

Amino acid sequence homology as used herein is similarly determined as the degree of identity between two sequences indicating a derivation of the first sequence from the second.

The present invention is also directed to variants of subtilisin Sub2 protease. The term "variant" refers to a polypeptide or protein having an amino acid sequence that differ to some extent from a native SEQ. ID. NO: 2, which is an amino acid sequence that vary from the native sequence by conservative amino acid substitutions, whereby one or more amino acids are substituted by another with same characteristics and conformational roles. The amino acid sequence variants possess substitutions, deletions, side-chain modifications and/or insertions at certain positions within the amino acid sequence of the native amino acid sequence. Conservative amino acid substitutions are herein defined as exchanges within one of the following five groups:

I. Small aliphatic, nonpolar or slightly polar residues: Ala, Ser, Thr, Pro, Gly
IL Polar, positively charged residues: His, Arg, Lys
III. Polar, negatively charged residues: and their amides: Asp, Asn, Glu, Gln
IV. Large, aromatic residues: Phe, Tyr, Trp
V. Large, aliphatic, nonpolar residues: Met, Leu, Ile, Val, Cys.

Figure 2:
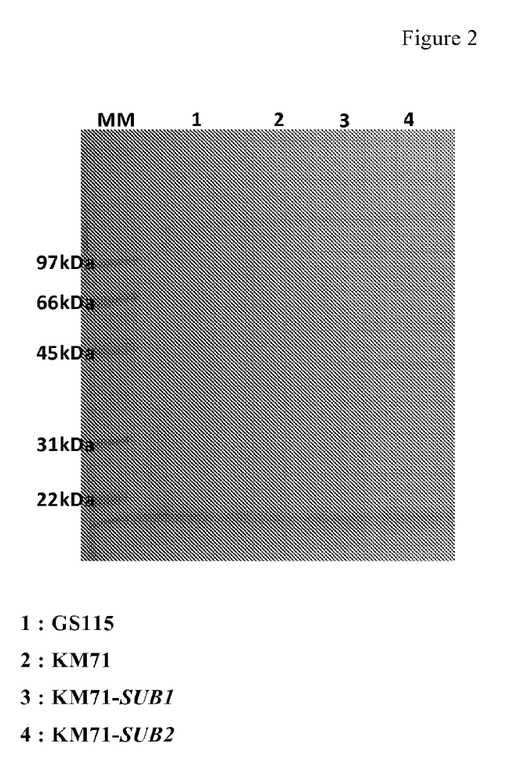
FIG. 2: Overexpression of *P. pastoris* SUB1 and SUB2 genes in *P. pastoris* KM71. Sub2 is over produced in *P. pastoris* KM71-SUB2
Figure 4:
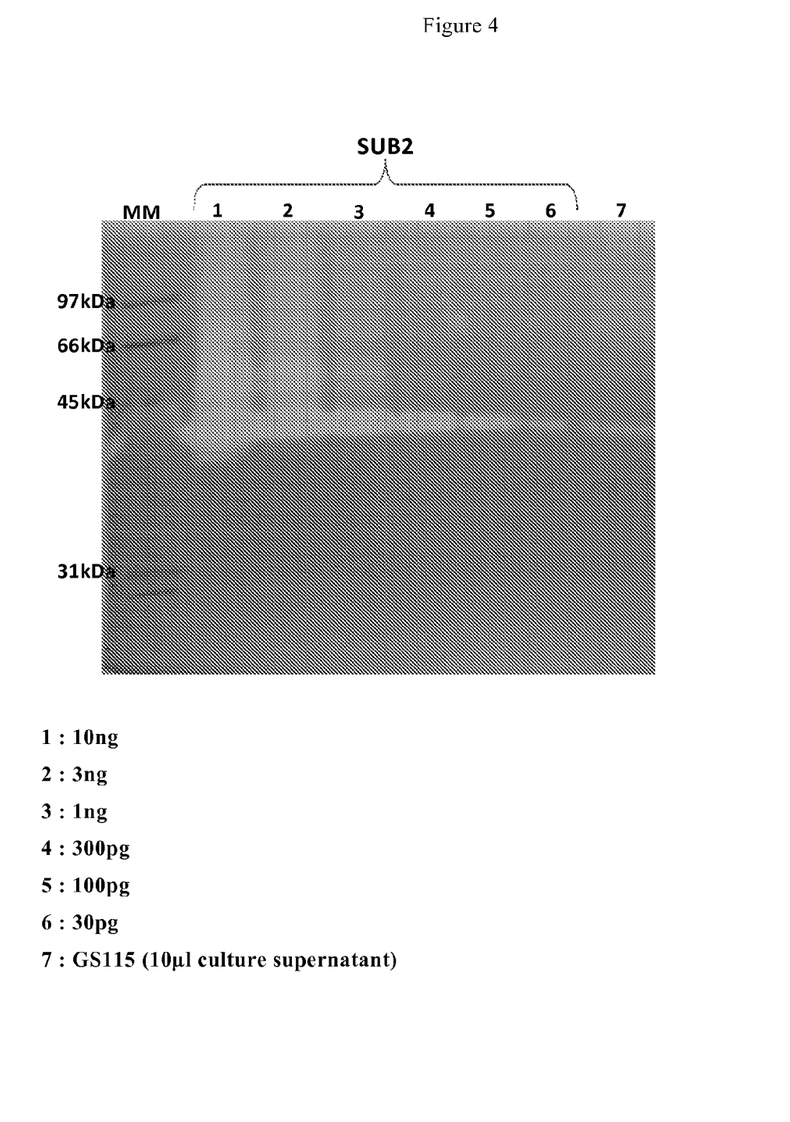
FIG. 4: Assessment of Sub2 amount secreted by *P. pastoris* GS115

*Pichia pastoris* DNAs encoding *P. pastoris* PrB (Sub1) and Sub2 were independently cloned in *Pichia pastoris* expression vectors and overexpressed in *Pichia pastoris*. The corresponding culture medium of *Pichia pastoris* grown in methanol inducing medium contained about 10 µg ml$^{-1}$ of 40 kDa Sub2 which could be detected on SDS-PAGE gels stained with Coomassie brilliant blue (FIG. 2, lane 4). Sub2 produced by gene overexpression had the same electrophoretic mobility than the enzyme secreted by GS115 strain (FIG. 4). The enzyme was active in Tris-HCl buffer between pH 7.0 and 9.5 on resorufin-labeled casein and keratine azure with a broad peak of optimum activity between pH 7.5 and 9.0. The specific activity measured using resorufin-labeled casein at pH=8.0 was similar for recombinant Sub3 and Sub4 (30 U/n).

Based on the nucleotide sequence of genomic DNA, Sub2 preproprotein is encoded by 1431 nucleotides starting from the ATG codon (477 aa). Based on alignment with different fungal subtilisins such as *Aspergillus fumigatus* ALP1 (Jaton-Ogay et al., 1992), the N-terminal aa sequence of the mature Sub2 is apparently preceded by a polypeptide of 179 aa, and the mature protein is 308 aa long. Inspection of the N-terminal aa sequence of the precursor beginning from the Met1 residue suggested the existence of a signal peptide in the protease precursor polypeptide with an hydrophobic core. Two putative signal peptidase cleavage sites in accordance with the −3-1 Von Heijne's rule were found after the Gly and Ala residues at position 16 and 18, respectively. The mature protein generated after cleavage of the pre and pro sequences from the 308 aa precursor have a calculated molecular mass of 34 kDa. The primary structure of the mature protein contains four N-linked glycosylation sequences Asn-X-Ser, However on SDS-PAGE gels, the protein is not reduced by endo-H treatment indicating that the enzyme is not glycosylated.

*Pichia pastoris* Cell Modification

In order that the gene for endogenous subtilisin Sub2 encoded by the DNA sequence comprising SEQ ID NO: 1, or variants or fragments thereof, is completely or partially inactivated, the *Pichia pastoris* cell is modified by recombinant DNA technology known to the person skilled in the art. Said recombinant DNA technology is, but not limited to, specific or random mutagenesis or specific deletion, insertion and/or substitution in DNA sequence SEQ ID NO: 1 encoding the gene for endogenous subtilisin Sub2, gene disruption or gene replacement techniques, anti-sense techniques, or a combination thereof.

The gene sequences (DNA sequences) respectively responsible for production of subtilsin Sub2 protease activity may be inactivated or partially or entirely eliminated. Thus, a *Pichia pastoris* cell of the invention expresses reduced or undetectable levels of subtilisin Sub2 protease or expresses functionally inactive subtilisin Sub2 protease.

In a particular embodiment, the said inactivation is obtained by modification of the respective structural or regulatory regions encoded within the subtilisin Sub2 protease genes of interest.

Mutagenesis may be performed using a suitable physical or chemical mutagenising agent. Examples of a physical or chemical mutagenising agent suitable for the present purpose include, but are not limited to, ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulfite, formic acid, and nucleotide analogues. When such agents are used, the mutagenesis is typically performed by incubating the cell to be mutagenised in the presence of the mutagenising agent of choice under suitable conditions, and selecting for cells showing a significantly reduced production of subtilisin Sub2.

Modification may also be accomplished by specific deletion, insertion and/or substitution in DNA sequence SEQ ID NO: 1 encoding the gene for endogenous subtilisin Sub2. This can be achieved by removal, introduction and/or substitution of one or more nucleotides in the structural sequence or a regulatory element required for the transcription or translation of the structural sequence. For example, nucleotides may be inserted or removed so as to result in the introduction of a stop codon, the removal of the start codon or a change of the open reading frame of the structural sequence. The modification or inactivation of the structural sequence or a regulatory element thereof may be accomplished by site-directed mutagenesis or PCR generated mutagenesis in accordance with methods known in the art.

The present invention provides a method for obtaining the *Pichia pastoris* cell of the invention, wherein the inactivation of the subtilisin Sub2 gene is obtained by:

i) cloning of the subtilisin Sub2 gene from *Pichia pastoris,*
ii) producing a DNA construct comprising the subtilisin Sub2 gene, wherein a part of said gene has been substituted, deleted, or extra DNA has been inserted within said subtilisin Sub2 gene,
iii) transforming said *Pichia pastoris* cell with the DNA constructs, and
iv) isolating transformants from which:
  1) no subtilisin Sub2 activity can be determined;
  2) a reduced level of subtilisin Sub2 activity can be determined; or 3) subtilisin Sub2 having lost its function can be obtained.

Although, in principle, the modification may be performed in vivo, i.e. directly on the cell expressing the subtilisin Sub2 protease genes, it is presently preferred that the modification be performed in vitro as exemplified below.

A convenient way to inactivate or reduce the subtilisin Sub2 protease production in a *Pichia pastoris* cell is based on techniques of gene interruption. In this method a DNA sequence corresponding to the endogenous gene or gene fragment of interest is mutagenised in vitro. Said DNA sequence thus encodes a defective gene which is then transformed into the host cell. By homologous recombination, the defective gene replaces the endogenous gene or gene fragment. It may be desirable that the defective gene or gene fragment also encodes a marker which may be used to select for transformants in which the respective gene encoding subtilisin Sub2 protease has been modified or destroyed.

Methods for deleting or disrupting a targeted gene are specifically described by Miller, et al (1985. Mol. Cell. Biol. 5:1714-1721); WO 90/00192; May, G. (1992. Applied Molecular Genetics of Filamentous Fungi. J. R. Kinghorn and G. Turner, eds., Blackie Academic and Professional, pp. 1-25); and Turner, G. (1994. Vectors for Genetic Manipulation. S. D. Martinelli and J. R. Kinghorn, eds., Elsevier, pp. 641-665).

Alternatively, the modification or inactivation of the DNA sequence may be performed by established anti-sense techniques using a nucleotide sequence complementary to an encoding sequence for subtilisin Sub2, e.g. the nucleotide sequences presented as SEQ. ID. No. 1. The anti-sense technology and its application is described in detail in U.S. Pat. No. 5,190,931 (University of New York).

The present invention provides also a method for obtaining the *Pichia pastoris* cell of the invention, wherein the inactivation of the subtilisin Sub2 gene is obtained by using anti-sense technology, said method comprising:
  i) construction of an expression plasmid resulting in the synthesis of a RNA molecule complementary to the mRNA transcribed from the subtilisin Sub2 gene;
  ii) transformation of said *Pichia pastoris* cell with said expression plasmid and a suitable marker;
  iii) selection of transformants using said marker; and
  iv) screening the selected transformants presenting reduction in the synthesis of the subtilisin Sub2 product.

Therefore, due to genetic modification, the *Pichia pastoris* host cell of the invention does not express subtilisin Sub2 protease or expresses significantly reduced levels of subtilisin Sub2 protease activity. In a preferred embodiment, the level of this proteolytic activity expressed by the *Pichia pastoris* host cell is individually reduced more than about 50%, preferably more than about 85%, more preferably more than about 90%, and most preferably more than about 95%. In another preferred embodiment, this proteolytic activity in the *Pichia pastoris* host cell of the invention may be reduced in any combination. In a most preferred embodiment, the product expressed by the *Pichia pastoris* host cell is essentially free from proteolytic activity due to subtilisin Sub2 protease.

Production of Heterologous Polypeptides

By the method of the invention, the proteolytic activity of subtilisin Sub2 protease is eliminated or significantly reduced, thereby improving the stability, purity and increasing the yield of susceptible polypeptides or proteins synthesized by the *Pichia pastoris* host cell of the invention.

The invention also provides a method of producing a heterologous polypeptide in the *Pichia pastoris* cell according to the invention, said method comprising:
  (a) introducing into said cell a nucleic acid sequence encoding for a polypeptide;
  (b) cultivating the cell of step (a) in a culture medium under conditions suitable for producing a polypeptide; and
  (c) recovering a polypeptide.

Another aspect of the invention provides also a method for improving the production of heterologous polypeptides by a *Pichia pastoris* cell comprising inactivating completely or partially the gene for endogenous subtilisin Sub2 encoded by the DNA sequence comprising SEQ ID NO: 1 in said *Pichia pastoris* cell.

Improving the production of heterologous polypeptides refers not only to increasing the yield of production of heterologous polypeptides of interest, but also to obtaining pure heterologous polypeptides, such as proteases, in the culture medium without a contaminating endogenous protease secreted by *Pichia pastoris*. This serves as a first step in purification of the expressed heterologous polypeptides.

The desired end product, i.e. the heterologous polypeptide or protein expressed by the *Pichia pastoris* cell of the invention, may be any polypeptides derived from prokaryotic sources, polypeptides derived from eukaryotic sources, and polypeptides derived from fungal sources other than the expression host.

As defined herein, a "heterologous polypeptide" is a protein or polypeptide gene product which is not native to the host cell, or is a native protein in which modifications have been made to alter the native sequence, or is a native protein whose expression is quantitatively altered as a result of a manipulation of a native regulatory sequence required for the expression of the native protein, such as a promoter, a ribosome binding site, etc., or other manipulation of the host cell by recombinant DNA techniques.

The terms "polypeptide" and "protein" used interchangeably herein, are polymers of amino acids which are covalently linked through peptide bonds. These polymers of amino acids can be of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. In addition, a polypeptide can be a phosphopolypeptide, glycopolypeptide or metallopolypeptide. Further, one or more polymer chains may be combined to form a polypeptide.

Heterologous polypeptides also include hybrid polypeptides which comprise a combination of partial or complete polypeptide sequences derived from at least two different polypeptides each of which may be homologous or heterologous with regard to the expression host.

Further, the heterologous polypeptides of the present invention also include: 1) naturally occurring allelic variations that may exist or occur in the sequence of polypeptides derived from the above prokaryotic, eukaryotic and final sources as well as those used to form the above hybrid polypeptides, and 2) engineered variations in the above heterologous polypeptides brought about, for example, by way of site specific mutagenesis wherein various deletions, insertions or substitutions of one or more of the amino acids in the heterologous polypeptides are produced.

Each of the above defined heterologous polypeptides is encoded by a heterologous DNA sequence which contains a stop signal which is recognized by the *Pichia pastoris* in which expression and secretion occurs. When recognized by those, the stop signal terminates translation of the mRNA encoding the heterologous polypeptide.

Preferably, the heterologous polypeptide is selected from the group consisting of therapeutic proteins, antibodies and enzymes. In another preferred embodiment the enzyme is a proteolytic enzyme or protease. In another specific embodiment, the heterologous polypeptide is a hormone.

Due to the absence of the subtilisin Sub2 protease activity, the heterologous protein expressed by the *Pichia pastoris* host cell may also be a precursor protein such as a zymogen, a hybrid protein, a protein obtained as a pro sequence or pre-pro sequence, or any other immature form.

The genetic design of the *Pichia pastoris* cell of the invention may be accomplished by the person skilled in the art using standard recombinant DNA technology for the transformation or transfection of a host cell (vide, e.g., Sambrook et al., inter alia).

The *Pichia pastoris* cell of the invention can further comprise a DNA sequence encoding for a heterologous polypeptide of interest.

Preferably, the *Pichia pastoris* cell is modified by methods known in the art for the introduction of an appropriate cloning vehicle, i.e. a plasmid or a vector, comprising a DNA sequence encoding for a heterologous polypeptide of interest. The cloning vehicle may be introduced into the *Pichia pastoris* host cell either as an autonomously replicating plasmid or integrated into the chromosome. Preferably, the cloning vehicle comprises one or more structural regions operably linked to one or more appropriate regulatory regions.

The vector may be a plasmid or simply a linear DNA fragment. Once transformed into *Pichia pastoris* host, the vector may integrate into the genome. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

"operably linked" when describing the relationship between two DNA regions simply means that they are functionally related to each other. For example, a pre-sequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The "structural regions" are regions of nucleotide sequences encoding the desired polypeptide. The regulatory regions include promoter regions comprising transcription and translation control sequences, terminator regions comprising stop signals, and polyadenylation regions. The promoter, i.e. a nucleotide sequence exhibiting a transcriptional activity in the host cell of choice, may be one derived from a gene encoding an extracellular or an intracellular protein, preferably therapeutic proteins, antibodies or enzymes; the enzymes preferably being proteases.

In order to produce secreted heterologous polypeptides using *Pichia pastoris*, the procedure consists of cloning the cDNA encoding the polypeptide of interest downstream of a signal sequence under the control of the AOX1 promoter in a *Pichia pastoris* expression vector. In general, the *Pichia pastoris* acid phosphatase gene (PHO1) signal sequence or the α-factor signal peptide sequence are used for entering the secretory pathway of the yeast (Higgins and Cregg, 1998). The construct which carries in addition to the cloned coding sequence of interest a gene for selection after transformation of *Pichia pastoris* is inserted into the *Pichia pastoris* genome at the AOX1 locus via homologous recombination. Selected transformants are screened for heterologous polypeptide production after induction of their encoding gene in a medium containing methanol.

The cloning vehicle may also include a selectable marker, such as a gene product which complements a defect in the host cell, or one which confers antibiotic resistance. Examples of antibiotics useful as *Pichia* selection markers include hygromycin, phlcomycin and basta.

Figure 5:
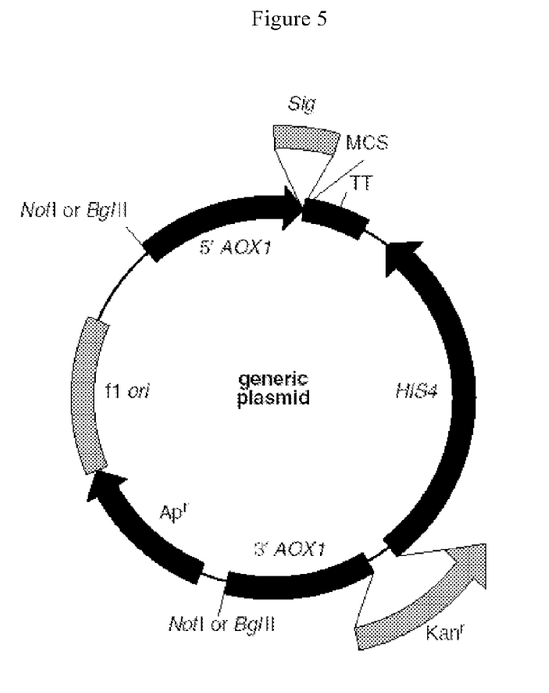
FIG. 5: Generic plasmid for heterologous polypeptide expression in *Pichia pastoris*. Elements present in all expression plasmids are shown in dark boxes, optional elements present in some plasmids are shown in gray boxes Abbreviation: TT, transcriptional termination sequence.

Typical plasmid designed for heterologous polypeptide expression in *Pichia pastoris* is illustrated in the generic plasmid shown in FIG. 5 (Higgins D. R., Current Protocols in Protein Science (1995)), wherein:

(1) The 5'$P_{AOX1}$ is the promoter from the *Pichia* alcohol oxidase (AOX1) gene; it is used to drive methanol-inducible expression of the gene of interest.

(2) The MCS is a multiple cloning site with unique restriction endonuclease sites; it is used to insert the gene of interest into the plasmid.

(3) Transcription termination sequences (TT) are derived from the native *Pichia* AUX1 gene; they are used to promote efficient mRNA processing and polyadenylation.

(4) HIS4, the wild-type gene for histidinol dehydrogenase, is a selectable marker; it is used to positively select for recombinant *Pichia* strains that have acquired the vector, which complements the auxotrophic his4 mutation.

(5) The 3'AOX1 sequence is derived from a region of the native gene that lies 3' to the transcription termination sequences; it is required for integration of vector sequence by gene replacement or gene insertion 3' to the chromosomal AOX1 gene.

(6) The ColE 1 origin of replication and ampicillin resistance gene ($Ap^r$) are required for replication and maintenance in bacteria.

(7) Unique restriction endonuclease sites are included that allow for the generation of linear plasmids that can integrate at the AOX1 locus by gene replacement (Nod and BglII). Other unique sites at 5 $P_{AOX1}$ (SacI and BstXI) and HIS4 (SalI and StuI) are included to allow generation of a linear plasmid that can integrate into the genome at these loci by gene insertion.

There are several additional features that are included in some expression vectors; these serve as tools for specialized functions. Sig is a DNA sequence juxtaposed between 5'$P_{AOX1}$ and the MCS region; it encodes a protein secretion signal that is expressed as an N-terminal fusion to the protein of interest. This sequence directs the passage of the protein through the secretory pathway and targets proteins that carry it out of the cell. Sig sequences that have been used for expression in *Pichia pastoris* include the *S. cerevisiae* mating type α prepro sequence (MF-1α prepro), the *Pichia* acidphosphatase signal sequence (PHO), the *S. cerevisiae* invertase signal sequence, and several hybrid sequences. Alternatively, the gene of interest may contain a sequence that encodes its own native secretion signal; that signal sequence may be functional in *Pichia*. $Kan^r$ is a bacterial kanamycin resistance gene; it may be included to confer resistance to the drug G418. Recombinant *Pichia* strains that contain multiple copies of $Kan^r$ are resistant to higher concentrations of G418 in a manner that correlates with the $Kan^r$ copy number. The f1 ori sequence is a bacterial single-strand origin of replication; this sequence can be included to generate single-stranded DNA in *Escherichia coli* to facilitate plasmid mutagenesis.

The procedures used to ligate the DNA construct of the invention, the promoter, terminator and other elements, respectively, and to insert them into suitable cloning vehicles containing the information necessary for replication, are well known to persons skilled in the art (Sambrook et al., 1989).

The present invention also encompasses simultaneously modifying *Pichia pastoris* cell (1) by recombinant DNA technologies (exemplified above) so that the gene for Sub2 is completely or partially inactivated and (2) by methods known in the art (exemplified above) for the introduction of an appropriate cloning vehicle, i.e. a plasmid or a vector, comprising a DNA sequence encoding for a heterologous polypeptide of interest.

The culture medium conditions suitable for producing a heterologous polypeptide may be any conventional medium suitable for culturing the *Pichia pastoris* host cell of the invention known to the person skilled in the art, and formulated according to the principles of the prior art. The medium preferably contains carbon and nitrogen sources as well as other inorganic salts. Suitable media, e.g. minimal or complex media, are available from commercial suppliers, or may be prepared according to published recipes, as in The Catalogue of Strains, published by The American Type Culture Collection. Rockville Md., USA. 1970. The culture conditions, such as temperature, pH and the like, are those previously used with the *Pichia pastoris* host cell and will be apparent to the person skilled in the art. Preferably the appropriate pH for fermentation is usually 6.0-8.0. For example, *Pichia pastoris* can be grown at 30° C. in glycerol-based yeast media [0.1 M potassium phosphate buffer at pH 6.0, containing 10 g/L yeast extract, 20 g/L peptone, 13 g/L yeast nitrogen base without amino acids (Becton-Dickinson, Sparks, Md.), 10 ml/L glycerol and 40 mg/L biotin]. *Pichia pastoris* cells are then harvested and resuspended in the same culture medium with methanol instead of glycerol and incubated for few more days, usually 2 days. Then, the culture supernatant is harvested after centrifugation at for example 3000×g, 4° C., 5 min.

After cultivation, the desired protein is recovered by conventional methods of protein isolation and purification from a culture medium. Well established purification procedures include separating the cells from the medium by centrifugation or filtration, precipitating proteinaceous components of the medium by means of a salt such as ammonium sulphate, and chromatographic methods such as ion exchange chromatography, gel filtration chromatography, affinity chromatography, and the like.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this specification, each of which is incorporated herein by reference in its entirety.

The foregoing description will be more fully understood with reference to the following Examples. Such Examples, are, however, exemplary of methods of practicing the present invention and are not intended to limit the scope of the invention.

EXAMPLES

Strains and Plasmids

*Pichia pastoris* GS115 and KM71 (Invitrogen) and plasmid pPICZA (Invitrogen) were used.
Native Secreted Subtilisin Production by Strains GS115 and KM71 (FIG. 1)

*Pichia pastoris* GS115 and KM71 as well as GS115 and KM71 transformants were grown to near saturation (OD=20 at 600 nm) at 30° C. in 10 ml of glycerol-based yeast media (0.1 M potassium phosphate buffer at pH 6.0, containing 1% (w/v) yeast extract, 2% (w/v) peptone, 1.34% (w/v) YNB without amino acids, 1% (v/v) glycerol and 4×10$^{-5}$% (w/v) biotin). Cells were harvested and resuspended in 2 ml of the same medium with 0.5% (v/v) methanol instead of glycerol and incubated for 2 days. The supernatant was then harvested and analyzed by SDS-PAGE (Laemmli, 1970) with a separation gel of 10% polyacrylamide. To detect proteolytic activity in culture supernatant, gelatine at a concentration of 0.1% was added in the gel. Gels were stained with Coomassie brilliant blue R-250 (Bio-Rad).
Construction of Strains GS115-sub2 and KM71-sub2

Two primers P1 (5'-GGYCACGGIACICACGTTGCIG-GIAC-3'; I is inosine) (SEQ ID NO: 5) and P2 (5'-GTGRG-GIGTIGCCATIGAIGTICC-3'; I is inosine) (SEQ ID NO: 6) were designed from alignment of genes encoding fungal subtilisins. Their nucleotide sequence encoded highly conserved amino acid sequences in subtilisin. PCR amplification of *Pichia pastoris* genomic DNA using these two primers revealed two 495 by products which could be distinguished by Bg111 digestion. Both fragments were separately cloned into the multiple cloning site of the pDrive vector using a PCR fragment cloning kit and sequenced. One fragment encoded part of the previously cloned gene encoding putative ppPRB. DNA sequencing of the other fragment revealed a sequence apparently encoding an amino acid sequence from another subtilisin. A DNA fragment harboring this sequence was recovered from the pDrive construct after BamHI-XhoI digestion and ligated to the large fragment of *Pichia pastoris* expression vector pPICZA cut with BglII and XhoI enzymes. The resulting plasmid (pKS1) (FIG. 6) corresponded to plasmid pPICZA in which the AOXJ promotor was replaced by part of the putative second *Pichia pastoris* subtilisin. pKS1 was cut by a Bsu96I (SauI) unique restriction site in the subtilisin DNA cloned fragment, and plasmidic linearized DNA was used to transform *Pichia pastoris* GS115 and KM71. Transformants were selected on YPD to which was added zeocin at a concentration of 100 μg/ml and subsequently screened for gelatinolytic activities on SDS-PAGE. One GS115 transformant among 10 showed no proteolytic component at 40 kDa. This clone was called GS115-sub2. Likewise, one KM71 transformant among eight showed no proteolytic component at 40 kDa. This clone was called KM71-sub2.

*Pichia pastoris* GS115-sub2 strain was deposited on 4 Dec. 2009 and has accession number THEM 23445.

DNA Sequence Encoding Sub2

Figure 6:
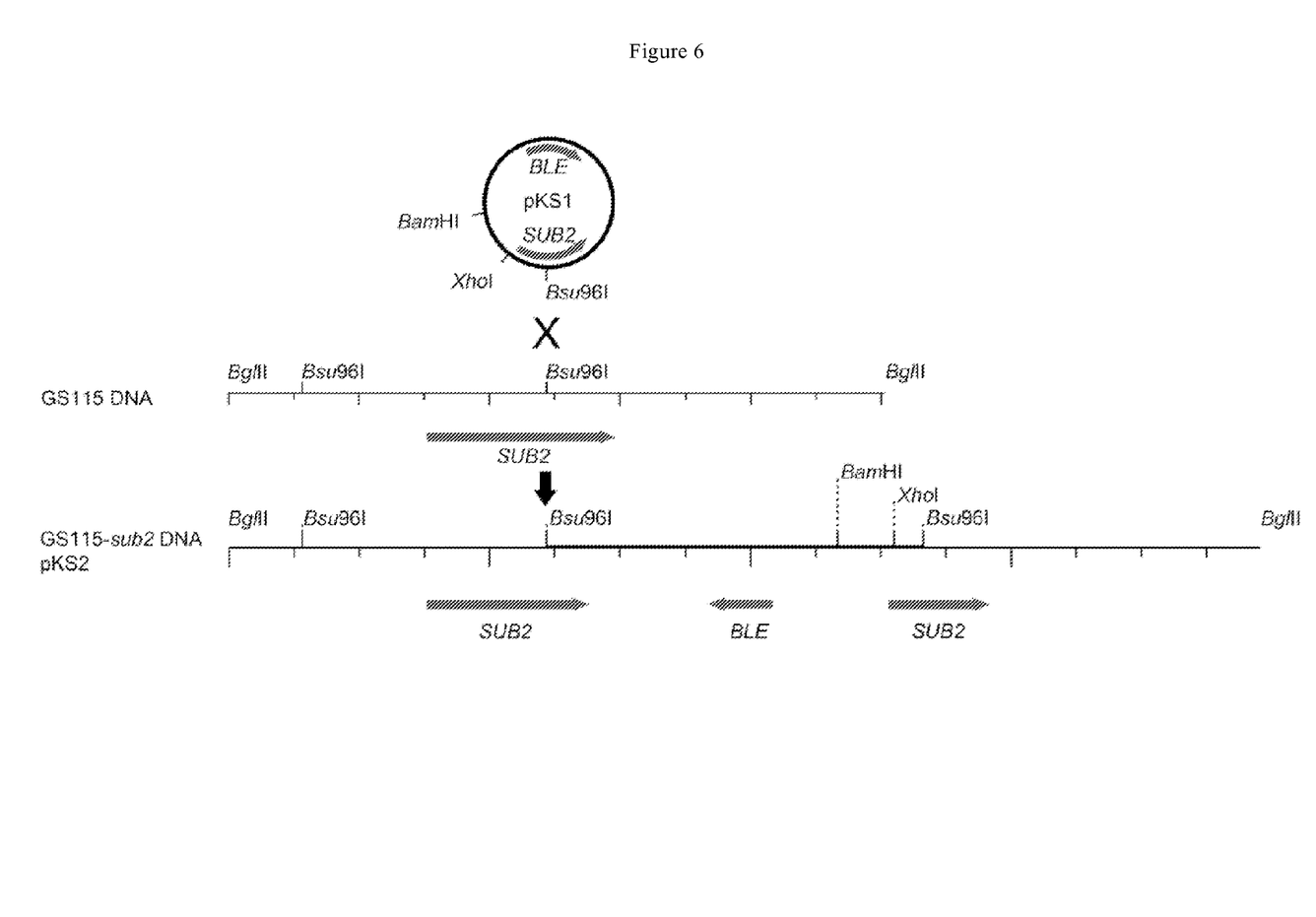
FIG. 6: Chromosomal integration of pKS1 in *Pichia pastoris* GS115 to generate GS115-sub2 strain. SUB2: Part of SUB2; BLE: *S. hindustanus* BLE gene for resistance to zeocin. Plasmid pKS2 sequence is 100% identical to GS115-sub2 DNA.

In order to clone full length Sub2 gene, one µg samples of GS115-sub2 genomic DNA were separately cut by different enzymes, relegated, and ligation products were used to transform *E. coli*. Five hygromycin resistant clones were shown to harbor a 8 kb plasmid called pKS2 (FIG. 6). Plasmid sequencing revealed two parts of a gene coding for the N- and the C-terminus of a subtilisin protease upstream and downstream of pPTCZA sequence, respectively.

Overproduction or Overexpression of *P. pastoris* SUB1 and SUB2 Genes (FIG. 2)

A SUB2 expression plasmid was constructed by cloning the PCR product in the multiple cloning site of the *E. coli-P. pastoris* shuttle vector pPICZA. DNA encoding Sub2 was amplified using primers P3: 5'-GTTTTCGAAGAAAT-GAAAATTATCAGATTAGCATCA-3' (SEQ ID NO:3) and P4: 5'-CTTCTCGAGTTAATAATCCCAAAATTCAGT-3' (SEQ ID NO:4), and *Pichia pastoris* genomic DNA as a target. The PCR product was purified using a PCR purification kit (Roche Diagnostics), digested by restriction enzymes SfuI and XhoI for which a recognition site was previously designed at the 5' extremity of the primers, and ligated to pPICZA cut with the same restriction enzymes SfuI and XhoI. The generated plasmid was called pKS129. *P. pastoris* KM71 was transformed by electroporation with 10 ng of pKS129 linearized by DraI as previously described. Transformants were selected on YPD to which was added zeocin at a concentration of 100 µg/ml and subsequently screened for Sub2 overproduction in culture supernatant. One clone among 10 showed was found to secrete Sub2 at a rate of 10 ng/ml. This clone was called KM71-SUB2.

Figure 3:
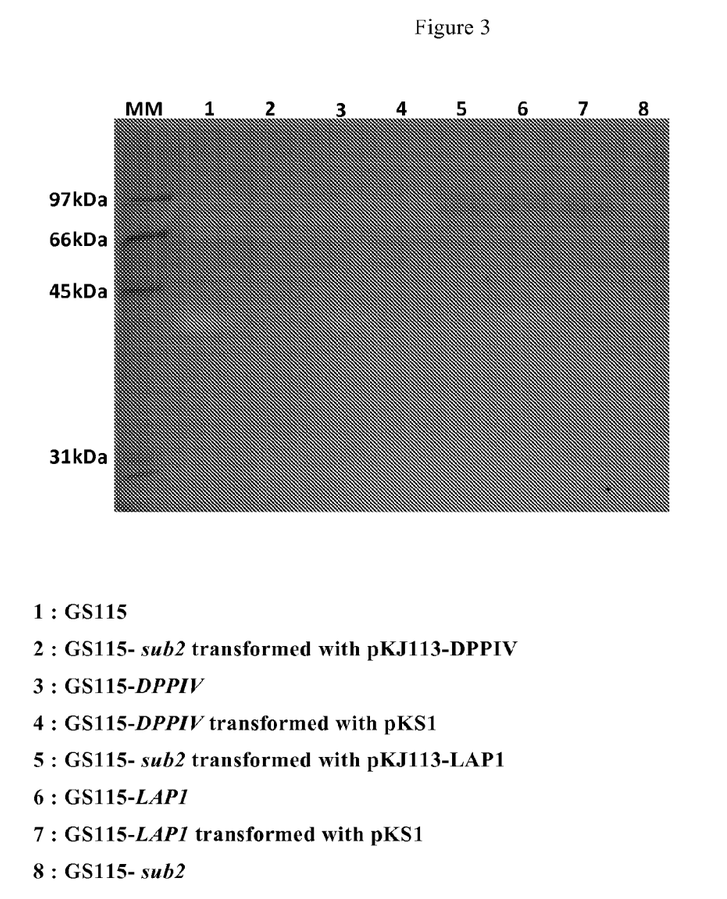
FIG. 3: Use of GS115-sub2 for heterologous protease production, (lanes 2 and 5), and SUB2 disruption in *P. pastoris* strains producing secreted proteases (lanes 4 and 7).

Use of GS115-sub2 for Heterologous Protease Production (FIG. 3)

Expression plasmids for recombinant *Aspergillus fumigatus* Lap1 and DppIV production were previously constructed by cloning cDNAs encoding the afore cited proteases in the *Pichia pastoris* expression vector pKJ113 (Beauvais et al., 1998; Monod et al., 2005). *Pichia pastoris* GS115-sub2 was transformed by electroporation as described in the Manual Version 2.0 of the *Pichia* Expression Kit (Invitrogen) with 10 µg of linearized DNA. Transformants selected on histidine-deficient medium [1 M sorbitol, 1% (w/v) dextrose, 1.34% (w/v) yeast nitrogen base (YNB) without amino acids, $4\times10^{-5}$% (w/v) biotin, $5\times10^{-3}$% amino acids (i.e. $5\times10^{-3}$% (w/v) of each L-glutamic acid, L-methionine, L-lysine, L-leucine, L-isoleucine)] were screened for insertion of the construct at the AOX1 site on minimal methanol plates [1.34% (w/v) YNB without amino acids, $4\times10^{-5}$% (w/v) biotin, 0.5% (v/v) methanol)].

Transformants unable to grow on media containing only methanol as a carbon source were assumed to contain the construct at the correct yeast genomic location by integration events in the AOX1 locus displacing the AOX1 coding region. The selected transformants were grown to near saturation (OD 20 at 600 nm) at 30° C. in 10 ml of glycerol-based yeast media (0.1 M potassium phosphate buffer at pH 6.0, containing 1% (w/v) yeast extract, 2% (w/v) peptone, 1.34% (w/v) YNB without amino acids, 1% (v/v) glycerol and $4\times10^{-5}$% (w/v) biotin). Cells were harvested and resuspended in 2 ml of the same medium with 0.5% (v/v) methanol instead of glycerol and incubated for 2 days. After 2 days of incubation, the supernatant was harvested and 10 µl were loaded on SDS-PAGE gels to identify clones expressing DppIV and Lap1. The lack of Sub2 secretion was checked in SDS-PAGE gels in which 0.1% gelatine was added.

SUB2 Disruption in *P. pastoris* Strains Producing Secreted Proteases (FIG. 3)

*Pichia pastoris* GS115-DPPIV and GS115-LAP1 producing *Aspergillus fumigatus* DppIV and Lap1, respectively, were previously constructed (Beauvais et al., 1998; Monod et al., 2005). GS115-DPPIV and GS115-LAP1 strains were transformed by pKS1 cut by at its unique Bsu96I (SauI) restriction site. Transformants were selected on YPD to which was added zeocin at a concentration of 100 µg/ml, and subsequently screened for gelatinolytic activities. One clone producing DppIV showing no proteolytic component at 40 kDa was retained and called GS115-DPPIV-sub2. One clone producing Lap1 showing no proteolytic component at 40 kDa was retained and called GS115-LAP1-sub2.

Assessment of Sub2 Amount Secreted by GS115 (FIG. 4)

Resorufin-labeled casein substrate was not sensitive enough to detect proteolytic activity in *Pichia pastoris* culture supernatants. Therefore, proteolytic activity of GS115 and KM71 culture supernatants were compared with serial dilution of purified recombinant Sub2 extract to assess the amount of protease secreted by the yeast (FIG. 4). One ml of culture supernatant was found to contain approximately 3 ng of Sub2. Increased activities were found in *Pichia pastoris* transformants producing various recombinant proteases (AfuDppIV and AfuLap1).

*Pichia pastoris* PRB Gene Cloning

Cloning experiments were performed before genome sequences were available. *Pichia pastoris* λEMBL3 genomic was constructed as previously described for *Candida parapsilosis* (de Viragh). Recombinant plaques ($2\times10^4$) of the genomic library were immobilized on GeneScreen nylon membranes (NEN Life Science products). The filters were hybridized with $^{32}$P-labelled *Saccharomyces cerevisiae* PRB DNA probe under low-stringency conditions (Monod et al., 1994). All positive plaques were purified and the associated bacteriophage DNAs were isolated as described previously (Grossberger, 1987). Agarose gel electrophoresis of restricted recombinant bacteriophage λEMBL3 DNA, Southern blotting and subcloning of hybridizing fragments from bacteriophages into pMTL21 or pUC19 were performed using standard protocols (Sambrook et al., 1989). DNA sequencing was performed by Microsynth (Balgach, Switzerland). PCR were performed with homologous primers designed on DNA sequences of different SUB genes.

Protein Extracts Analysis

Extracts were analyzed by SDS-PAGE (Laemmli, 1970) with a separation gel of 12% polyacrylamide. To detect proteolytic activity of culture supernatant in gels, gelatin at a concentration of 0.1% was added in the gel. In this case, 10 µl of *P. pastoris* culture supernatant were treated with an equal volume of SDS-PAGE sample buffer without beta-mercaptoethanol (125 mM Tris, pH 6.8, 4% SDS, 20% glycerol, 0.002 bromophenol blue), and the mixture was loaded without further treatment and no heating onto SDS-PAGE gels. After electrophoresis, the gels were incubated for 1 h at room temperature in 10 volumes of 2.5% Triton X-100 under constant agitation. The gels were then incubated overnight at room temperature and 10 mM sodium phosphate buffer, pH 7.0 or pH 4.0. The gels were stained 30 min with 0.1% Coomassie Brilliant blue R-250 (Bio-Rad) in ethanol-acetic acid-water (40:10:50) and destained in the same solvent.

The invention claimed is:

1. A recombinant *Pichia pastoris* cell wherein a gene for endogenous subtilisin Sub2 encoded by a DNA sequence comprising SEQ ID NO: 1 is completely or partially inactivated.

2. The recombinant *Pichia pastoris* cell of claim 1, wherein the cell is made recombinant by specific mutagenesis.

3. The recombinant *Pichia pastoris* cell of claim 1, wherein the *Pichia pastoris* cell further comprises a DNA sequence encoding for a heterologous polypeptide.

4. The *Pichia pastoris* cell of claim 2, wherein the heterologous polypeptide is selected from the group consisting of a therapeutic protein, an antibody and an enzyme.

5. A method of producing a heterologous polypeptide in the recombinant *Pichia pastoris* cell according to claim 1, the method comprising:
   (a) introducing into the cell a nucleic acid sequence encoding for a polypeptide;
   (b) cultivating the cell of step (a) in a culture medium under conditions suitable for producing the polypeptide; and
   (c) recovering the polypeptide.

6. A method for improving the production of a heterologous polypeptide by a *Pichia pastoris* cell comprising inactivating completely or partially a gene for endogenous subtilisin Sub2 encoded by a DNA sequence comprising SEQ ID NO: 1 in the *Pichia pastoris* cell.

* * * * *

SEQUENCE LISTING

<160> NUMBER OF SEQ ID NOS: 6

<210> SEQ ID NO 1
<211> LENGTH: 1434
<212> TYPE: DNA
<213> ORGANISM: Pichia pastoris

<400> SEQUENCE: 1

```
atgaaaatta tcagattagc atcagtggct accgtggcta ccctggcaca ctcgcttttg      60
ataccatctc ttgaccaatt gaatatccaa ttgccgtttt ccttgcccca tcatactgag     120
tctccatcgc tgaaattaca gggatctaac ccatttgaat cttccacagt gagacccgac     180
cctatccaga tatattcgac tggatataag gtgattgaga actcctatat tgtcactgta     240
gacagttcca tcactgattc ggaacttcag cagctttatg actacattaa aggtggatac     300
gaattcatgt tgaacaatga agacccctttt tcgttgccca tgggtattaa gagactaccc     360
aagcattctt tgtttgaacc tttcagtatc ggtgactcca tgaaaggctt tgtcggtttc     420
tttccaccaa gactagttga aaaactggcc tctatggacc ttcctatagt ggctatcgag     480
gcagattcag tagtccattc gacaaaagag tacgcagttg acgaacatgt aacctggggt     540
ttggctagaa tttcccagag gcaaacacta gataccaata gaattatat ataccatgtc     600
gatggtggca aaaatgttac cgcctatgtc atcgacactg gtattttttgt tgaccatgaa     660
cagtttgaaa agcgggctcg ttggggtgca actatcccat ttggggacgt tgacaaggat     720
gccaatggac acggaactca tgtggctggt acaatcggtt ccgcaaaata tggtgtggct     780
aaacagactt cactggtggc agtaaaggtg ctcaactctg atgggactgg caccctttca     840
gatgtcatta aggcattga gtttgtggtc aaagaccaca gagctcaag gggcaagtct     900
aagggctctg ttgctaacat gtccttaggt ggtggtctgt cagttgctct cacatacgct     960
gtaaatgctg ctgttgataa tggcatccac tttgccgtag ccgctggaaa tgacaatgct    1020
aacgcttgca gttactctcc agcaaattca gctaaggcaa tcactgcagc tgcctctact    1080
gtcgaggacg aacgtgcgtt cttcagtaac tggggtacct gtgtggacgt ctttgcccca    1140
gggtatctta ttgagtccac ctacattggc cttccaacct ccacaagagt tctttcgggt    1200
acttcgatgg cctctccaca cgttgccggt cttttgagtt actacctctc tctacaaccc    1260
gggcatgaat cgcaatataa ctccggtgac tcattgaccc cagctcaact aaaagctagg    1320
attttgagtt tcagtaccaa ggatgtactt gatgactcgg atctaaacta tggcactcct    1380
aacttgctaa tctacaactc aagagacaac attactgaat tttgggatta ttaa          1434
```

<210> SEQ ID NO 2
<211> LENGTH: 477
<212> TYPE: PRT
<213> ORGANISM: Pichia pastoris

<400> SEQUENCE: 2

```
Met Lys Ile Ile Arg Leu Ala Ser Val Ala Thr Val Ala Thr Leu Ala
1               5                   10                  15

His Ser Leu Leu Ile Pro Ser Leu Asp Gln Leu Asn Ile Gln Leu Pro
            20                  25                  30

Phe Ser Leu Pro His His Thr Glu Ser Pro Ser Leu Lys Leu Gln Gly
        35                  40                  45

Ser Asn Pro Phe Glu Ser Ser Thr Val Arg Pro Asp Pro Ile Gln Ile
    50                  55                  60
```

-continued

```
Tyr Ser Thr Gly Tyr Lys Val Ile Glu Asn Ser Tyr Ile Val Thr Val
 65                  70                  75                  80

Asp Ser Ser Ile Thr Asp Ser Glu Leu Gln Gln Leu Tyr Asp Tyr Ile
                 85                  90                  95

Lys Gly Gly Tyr Glu Phe Met Leu Asn Asn Glu Asp Pro Phe Phe Val
            100                 105                 110

Ala Met Gly Ile Lys Arg Leu Pro Lys His Ser Leu Phe Glu Pro Phe
        115                 120                 125

Ser Ile Gly Asp Ser Met Lys Gly Phe Val Gly Phe Phe Pro Pro Arg
    130                 135                 140

Leu Val Glu Lys Leu Ala Ser Met Asp Leu Pro Ile Val Ala Ile Glu
145                 150                 155                 160

Ala Asp Ser Val Val His Ser Thr Lys Glu Tyr Ala Val Asp Glu His
                165                 170                 175

Val Thr Trp Gly Leu Ala Arg Ile Ser Gln Arg Gln Thr Leu Asp Thr
            180                 185                 190

Asn Arg Asn Tyr Ile Tyr His Val Asp Gly Gly Lys Asn Val Thr Ala
        195                 200                 205

Tyr Val Ile Asp Thr Gly Ile Phe Val Asp His Glu Gln Phe Glu Lys
210                 215                 220

Arg Ala Arg Trp Gly Ala Thr Ile Pro Phe Gly Asp Val Asp Lys Asp
225                 230                 235                 240

Ala Asn Gly His Gly Thr His Val Ala Gly Thr Ile Gly Ser Ala Lys
                245                 250                 255

Tyr Gly Val Ala Lys Gln Thr Ser Leu Val Ala Val Lys Val Leu Asn
            260                 265                 270

Ser Asp Gly Thr Gly Thr Leu Ser Asp Val Ile Lys Gly Ile Glu Phe
        275                 280                 285

Val Val Lys Asp His Lys Ser Ser Arg Gly Lys Ser Lys Gly Ser Val
    290                 295                 300

Ala Asn Met Ser Leu Gly Gly Gly Leu Ser Val Ala Leu Thr Tyr Ala
305                 310                 315                 320

Val Asn Ala Ala Val Asp Asn Gly Ile His Phe Ala Val Ala Ala Gly
                325                 330                 335

Asn Asp Asn Ala Asn Ala Cys Ser Tyr Ser Pro Ala Asn Ser Ala Lys
            340                 345                 350

Ala Ile Thr Ala Ala Ala Ser Thr Val Glu Asp Glu Arg Ala Phe Phe
        355                 360                 365

Ser Asn Trp Gly Thr Cys Val Asp Val Phe Ala Pro Gly Tyr Leu Ile
    370                 375                 380

Glu Ser Thr Tyr Ile Gly Leu Pro Thr Ser Thr Arg Val Leu Ser Gly
385                 390                 395                 400

Thr Ser Met Ala Ser Pro His Val Ala Gly Leu Leu Ser Tyr Tyr Leu
                405                 410                 415

Ser Leu Gln Pro Gly His Glu Ser Gln Tyr Asn Ser Gly Asp Ser Leu
            420                 425                 430

Thr Pro Ala Gln Leu Lys Ala Arg Ile Leu Ser Phe Ser Thr Lys Asp
        435                 440                 445

Val Leu Asp Asp Ser Asp Leu Asn Tyr Gly Thr Pro Asn Leu Leu Ile
    450                 455                 460

Tyr Asn Ser Arg Asp Asn Ile Thr Glu Phe Trp Asp Tyr
465                 470                 475
```

<210> SEQ ID NO 3

```
<211> LENGTH: 36
<212> TYPE: DNA
<213> ORGANISM: Artificial
<220> FEATURE:
<223> OTHER INFORMATION: synthetic sequence

<400> SEQUENCE: 3
gttttcgaag aaatgaaaat tatcagatta gcatca                              36

<210> SEQ ID NO 4
<211> LENGTH: 30
<212> TYPE: DNA
<213> ORGANISM: Artificial
<220> FEATURE:
<223> OTHER INFORMATION: synthetic sequence

<400> SEQUENCE: 4
cttctcgagt taataatccc aaaattcagt                                     30

<210> SEQ ID NO 5
<211> LENGTH: 26
<212> TYPE: DNA
<213> ORGANISM: Artificial
<220> FEATURE:
<223> OTHER INFORMATION: Synthetic sequence
<220> FEATURE:
<221> NAME/KEY: n
<222> LOCATION: (9)..(9)
<223> OTHER INFORMATION: inosine
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: n
<222> LOCATION: (12)..(12)
<223> OTHER INFORMATION: inosine
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: n
<222> LOCATION: (18)..(18)
<223> OTHER INFORMATION: inosine
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: n
<222> LOCATION: (21)..(21)
<223> OTHER INFORMATION: inosine
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: n
<222> LOCATION: (24)..(24)
<223> OTHER INFORMATION: inosine
<220> FEATURE:
<221> NAME/KEY: misc_feature
<222> LOCATION: (24)..(24)
<223> OTHER INFORMATION: n is a, c, g, or t

<400> SEQUENCE: 5
ggycacggna cncacgtngc nggnac                                         26

<210> SEQ ID NO 6
<211> LENGTH: 24
<212> TYPE: DNA
<213> ORGANISM: Artificial
<220> FEATURE:
```

```
<223> OTHER INFORMATION: Synthetic sequence
<220> FEATURE:
<221> NAME/KEY: n
<222> LOCATION: (7)..(7)
<223> OTHER INFORMATION: inosine
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: n
<222> LOCATION: (10)..(10)
<223> OTHER INFORMATION: inosine
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: n
<222> LOCATION: (16)..(16)
<223> OTHER INFORMATION: inosine
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: n
<222> LOCATION: (19)..(19)
<223> OTHER INFORMATION: inosine
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: n
<222> LOCATION: (22)..(22)
<223> OTHER INFORMATION: inosine
<220> FEATURE:
<221> NAME/KEY: misc_feature
<222> LOCATION: (22)..(22)
<223> OTHER INFORMATION: n is a, c, g, or t

<400> SEQUENCE: 6
gtgrggngtn gccatngang tncc                                          24
```